(12) United States Patent
Chrusciel et al.

(10) Patent No.: US 9,489,491 B2
(45) Date of Patent: Nov. 8, 2016

(54) PORTABLE AND MODULAR PRESCRIPTION DRUG DISPENSING DEVICE

(71) Applicant: Norwich University, Northfield, VT (US)

(72) Inventors: Nicole M. Chrusciel, New Britain, CT (US); Jeremy A. Hansen, Berlin, VT (US)

(73) Assignee: Norwich University, Northfield, VT (US)

(*) Notice: Subject to any disclaimer, the term of this patent is extended or adjusted under 35 U.S.C. 154(b) by 130 days.

(21) Appl. No.: 13/946,817

(22) Filed: Jul. 19, 2013

(65) Prior Publication Data
US 2014/0214200 A1     Jul. 31, 2014

Related U.S. Application Data

(60) Provisional application No. 61/673,338, filed on Jul. 19, 2012.

(51) Int. Cl.
| | |
|---|---|
| *G06F 7/00* | (2006.01) |
| *G06F 19/00* | (2011.01) |
| *A61J 7/04* | (2006.01) |
| *A61J 7/00* | (2006.01) |

(52) U.S. Cl.
CPC .......... *G06F 19/3462* (2013.01); *A61J 7/0076* (2013.01); *A61J 7/0481* (2013.01); *A61J 7/0418* (2015.05); *A61J 2205/20* (2013.01); *A61J 2205/70* (2013.01)

(58) Field of Classification Search
USPC ........................................................ 700/237
See application file for complete search history.

(56) References Cited

U.S. PATENT DOCUMENTS

| | | | | |
|---|---|---|---|---|
| 3,687,336 A * | 8/1972 | Gayle | ....................... | A61J 7/04 110/308 |
| 4,823,982 A * | 4/1989 | Aten | ......................... | A61J 7/04 221/129 |
| 6,004,020 A * | 12/1999 | Bartur | ................... | A61J 7/0481 221/123 |
| 6,318,051 B1* | 11/2001 | Preiss | ............................. | 53/493 |
| 2009/0105876 A1* | 4/2009 | Simpson | ............... | A61J 7/0084 700/242 |
| 2009/0223994 A1* | 9/2009 | Getz | ..................... | A61J 7/0076 221/154 |
| 2010/0305750 A1* | 12/2010 | Conley | ................. | A61J 7/0481 700/237 |

* cited by examiner

*Primary Examiner* — Kyle Logan
(74) *Attorney, Agent, or Firm* — James Marc Leas

(57) ABSTRACT

A dispensing device for dispensing doses of non-individually packaged pills at a plurality of pre-specified dosing times includes a housing that holds a removable magazine, a dispensing unit and an electronic circuit. The removable magazine is configured to hold a stack of the non-individually packaged pills. The dispensing unit is configured to operate on the removable magazine to dispense a pre-specified dose of the pills upon receipt of a signal. The electronic circuit includes a timer that provides the signal at the pre-specified dosing times to activate the dispensing unit to dispense the pre-specified dose.

15 Claims, 15 Drawing Sheets

Position 1

Position 2

Position 3

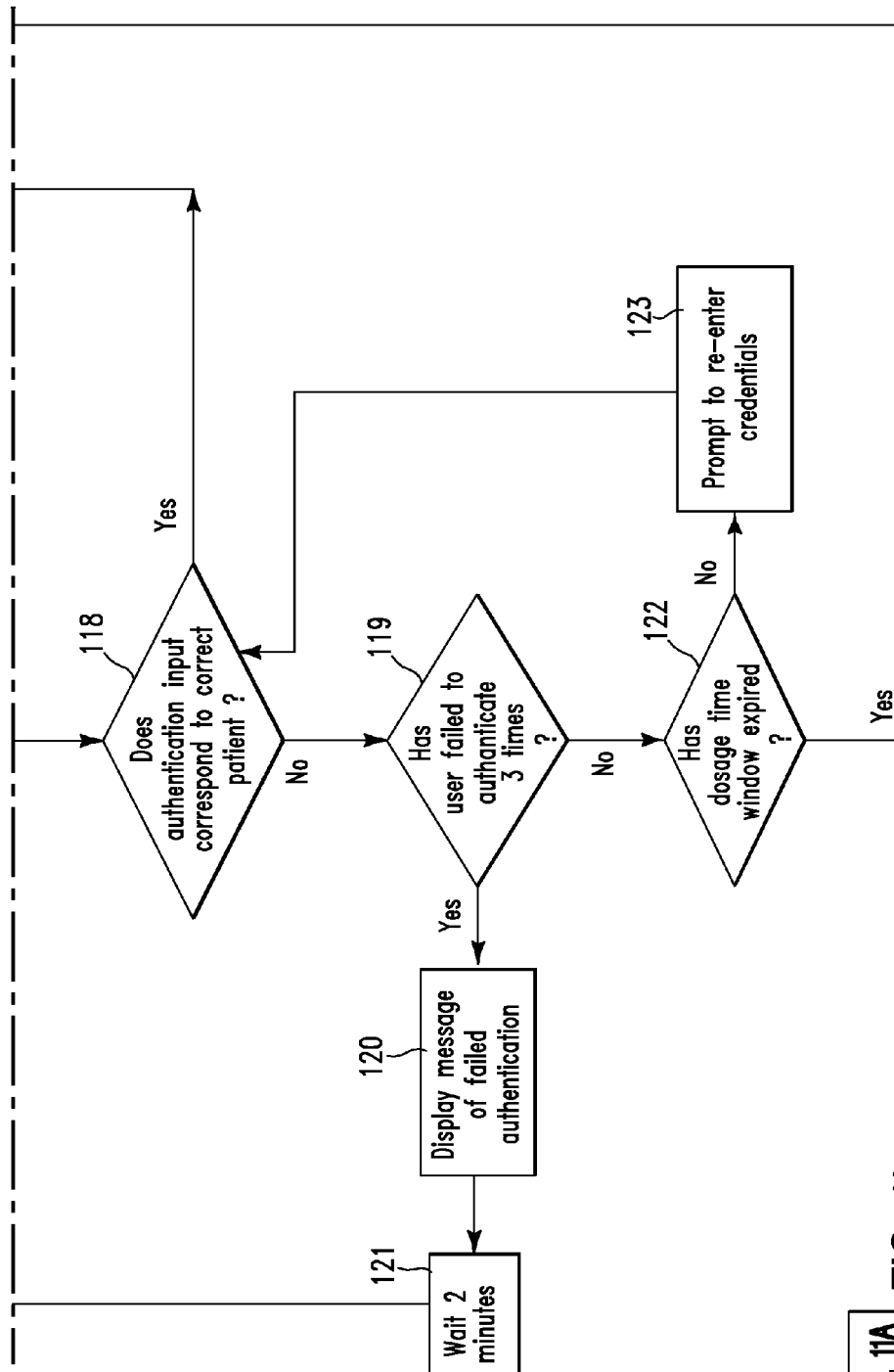

PORTABLE AND MODULAR PRESCRIPTION DRUG DISPENSING DEVICE

PRIORITY

This application claims the benefit of U.S. Provisional Patent Application 61/673,338, filed Jul. 19, 2012, "Portable and Modular Prescription Drug Dispensing Device," incorporated herein by reference.

FIELD

This patent application generally relates to a scheme for dispensing pills.

BACKGROUND

Preventing errors in dispensing, taking, and monitoring prescription drugs has been needed to prevent incorrect drug taking, overdose, and theft, and to ensure correct dosage and timing. Applicants recognized that better schemes than those available are needed and such solutions are provided by the following description.

SUMMARY

One aspect of the present patent application is a dispensing device for dispensing doses of non-individually packaged pills at a plurality of pre-specified dosing times. The device includes a housing that holds a removable magazine, a dispensing unit and an electronic circuit. The removable magazine is configured to hold a stack of the non-individually packaged pills. The dispensing unit is configured to operate on the removable magazine to dispense a pre-specified dose of the pills upon receipt of a signal. The electronic circuit includes a timer that provides the signal at the pre-specified dosing times to activate the dispensing unit to dispense the pre-specified dose.

Another aspect is a dispensing device for dispensing doses of pills at a plurality of pre-specified dosing times. The device includes a housing that holds a removable magazine, a dispensing unit, a tamper recognizing device, and an electronic circuit. The removable magazine is configured to hold a stack of the pills. The dispensing unit is configured to operate on the removable magazine to dispense a pre-specified dose of the pills upon receipt of a signal. The electronic circuit includes a timer that provides the signal at the pre-specified dosing times to activate the dispensing unit to dispense the pre-specified dose. The tamper recognizing device includes a scheme that recognizes the occurrence of tampering and provides an action in response to the occurrence of tampering.

Another aspect is a dispensing device for dispensing doses of pills at a plurality of pre-specified dosing times. The device includes a housing that holds a removable magazine, a dispensing unit, an authentication device, and an electronic circuit. The removable magazine is configured to hold a stack of the pills. The dispensing unit is configured to operate on the removable magazine to dispense a pre-specified dose of the pills upon receipt of a signal. The electronic circuit includes a timer that provides the signal at the pre-specified dosing times to activate the dispensing unit to dispense the pre-specified dose upon authorization by the authentication device. The authentication device includes a scheme for receiving identifying data from a current user, comparing the current user identifying data with previously stored identifying data, and authorizing dispensing a dose if the current user identifying data sufficiently matches the previously stored identifying data.

BRIEF DESCRIPTION OF THE DRAWINGS

The foregoing will be apparent from the following detailed description, as illustrated in the accompanying drawings, in which:

FIG. 2a is a three dimensional view of a removable magazine for use with the housing of FIG. 1a;

FIG. 2d is a three dimensional view of a rotating foot, its motor, and the shaft there between;

FIG. 4 is a three dimensional view of a removable magazine with back panel removed for use with the housing of FIG. 1a;

FIGS. 5a-5f are three dimensional views showing positions of a sliding plate that operates on pills stacked in the removable magazine of FIG. 2a;

FIG. 11, including FIGS. 11a-11b, is a flow chart showing a program for each removable magazine that may be inserted into the housing; and FIG. 12, including

DETAILED DESCRIPTION

The present applicants created a system for dispensing doses of non-individually packaged pills at pre-specified dosing times. In one embodiment the system includes a housing that holds a removable magazine, a dispensing unit and an electronic circuit. The removable magazine holds a stack of the non-individually packaged pills. The dispensing unit operates on the removable magazine to dispense a pre-specified dose of the pills. The electronic circuit includes a timer that provides a signal to activate the dispensing unit to dispense a specified dose at each of the pre-specified dosing times.

In one embodiment the housing includes two or more of the removable magazines in which each of the removable magazines is configured to hold a stack of the non-individually packaged pills. In one embodiment, each of these removable magazines is configured to hold a different kind of pill. In one embodiment, each of the removable magazines is configured to hold a sufficient number of pills of a single type to provide a specified dose at several dosing times.

In one embodiment the system optionally includes an authentication device that includes a scheme for receiving identifying data from a current user, comparing the current user identifying data with previously stored identifying data, and authorizing dispensing a dose if the current user identifying data sufficiently matches the previously stored identifying data.

In one embodiment the system optionally includes a tamper recognizing device that includes sensors that recognize the occurrence of tampering.

The authentication device and the tamper recognizing device can be included separately or together. Either or both can be included with the timer that provides a signal to activate the dispensing unit to dispense a specified dose at each of the pre-specified dosing times. Any one, or any two or all three of these can be combined with the housing that includes a single magazine or multiple magazines.

Figure 1A:
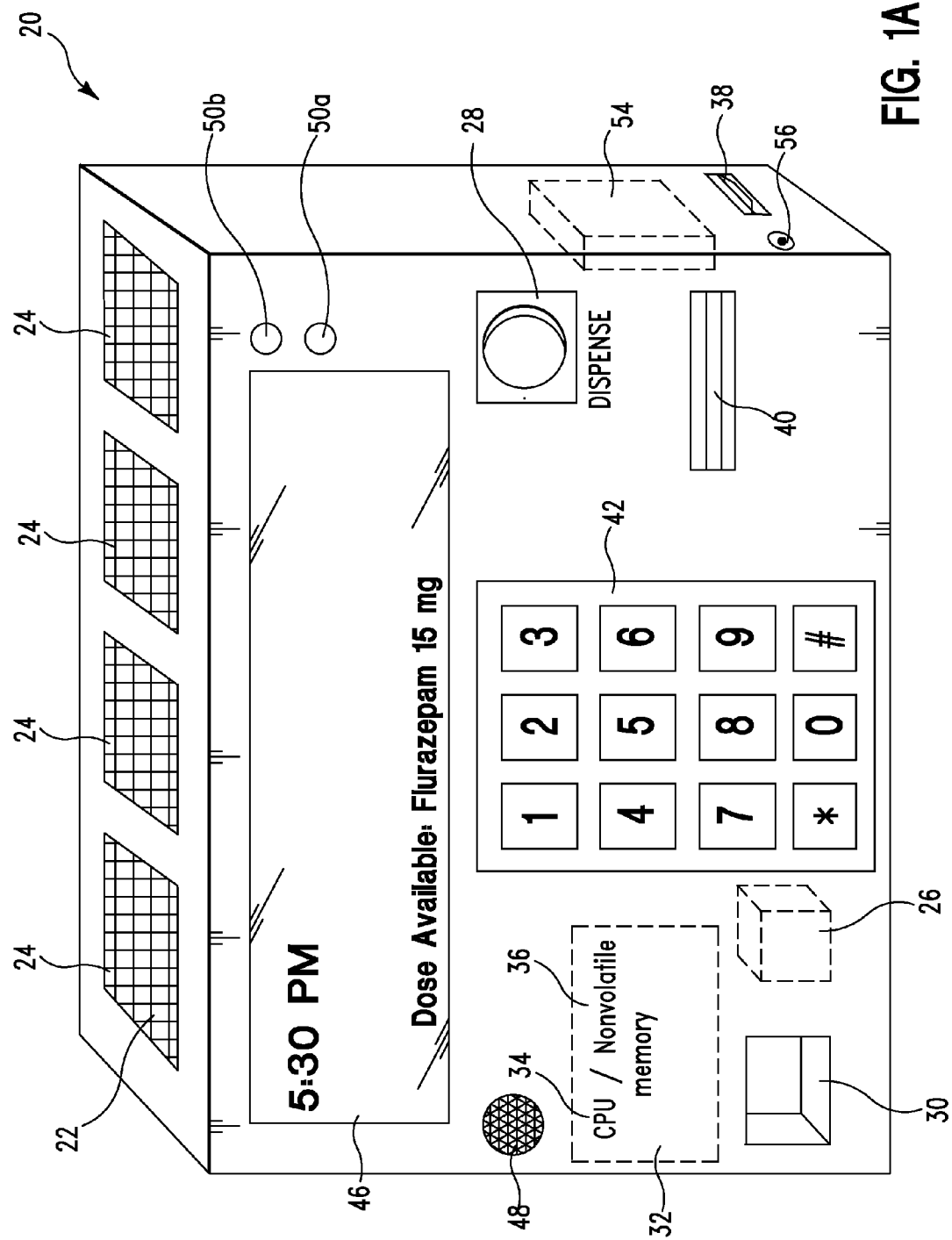
FIG. 1a is a three dimensional view of a housing of the present patent application showing the slots for removable pill magazines, the dispensing outlet, the motor, the dispense button, an electronic circuit that includes a central processing unit and memory, a micro-USB port, a fingerprint scanner, a keypad, an LCD screen, a buzzer/speaker, red and green LED's, a rechargeable battery pack and a plug.
Figure 1B:
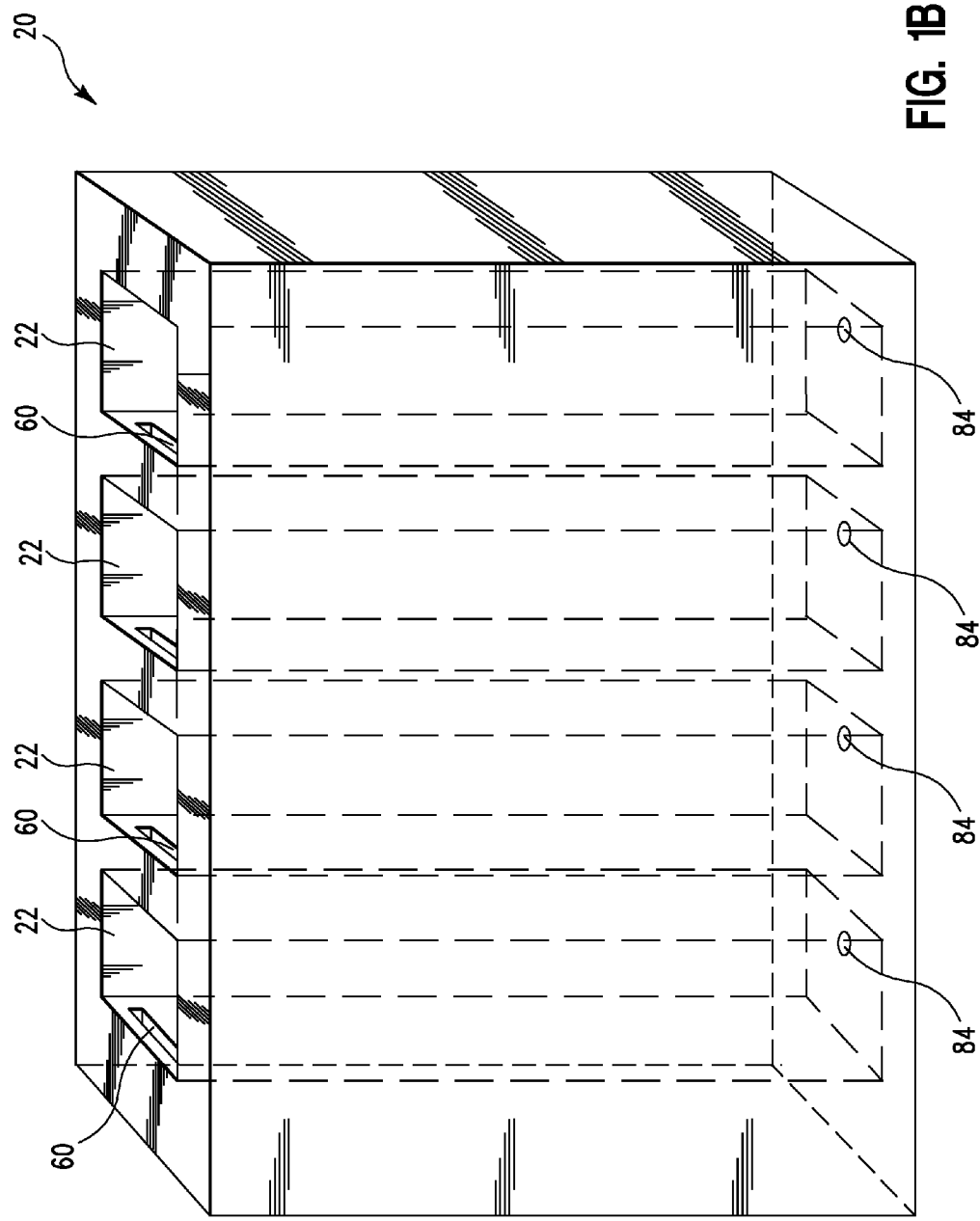
FIG. 1b is a three dimensional x-ray view of the housing of FIG. 1a showing the slots for pill magazines.

Housing 20 includes slots 22 with removable magazines 24 inserted, as shown in FIGS. 1a, 1b. Housing 20 also includes a dispensing unit that operates on removable magazines 24 to dispense one or more pills. The dispensing unit includes dispensing outlet 30. The dispensing unit may also includes motor 26 and dispense button 28. Motor 26 is connected to cause housing 20 to vibrate. It can optionally be used during dispensing to facilitate movement of pills. Dispense button 28 is optional if authentication is included.

Electronic circuit 32 includes central processing unit 34 and memory, such as non-volatile memory 36, that receives a program setting timing for dispensing pills and stores data about authentication, tampering, and time a pill was actually dispensed.

Communications, such as through micro-USB port 38 provides for programming times at which pills will be dispensed from each magazine. Communications may be two-way, allowing information, such as times pills were actually dispensed and authentication and tampering data can be output. In addition, micro-USB port 38 may provide for programming and updating software. Firewire, Wi-Fi, Blue tooth, GSM, 3G/4G, wireless USB, and mobile ad-hoc networks can be used in addition to or instead of the micro-USB port.

An authentication system such as fingerprint scanner 40 may be included to ensure that the correct person is receiving the pill. In one alternative, the patient can use an input device, such as keypad 42, to input a password. Voice recognition, physical tokens/keys, or facial recognition can also be used. These methods can be used individually or in any combination to authenticate the user.

Output devices, such as LCD screen 46, buzzer/speaker 48, and red and green LED's 50a, 50b can optionally be included to allow communication from the device to the patient. Dispense motor 26 that causes the housing to vibrate, can also optionally be used to alert the user. Projectors, external displays, remote notifications, and devices that provide other sensory stimulation can also be used. For example such communications may indicate the name of the medication, the time for the next dose, dosage instructions, and side effects. An input device, such as keypad 42, allows the patient, pharmacist, doctor, patient, caregiver, or other personnel to input information to the device. The input device can also be a wired or wireless computer mouse, a trackball, a gesture recognition device, a touchscreen, a brain-computer interface, a neural interface, foot pedals, a sip-and-puff (SNP) controller, a mouthstick, a head controller, a chin controller, a speech controller, or a tongue controller.

A power supply, such as rechargeable battery pack 54 and/or plug 56 for receiving external power from a wall outlet and an external power supply are also included. Micro-USB port 38 can also be used for charging the internal battery.

Figure 2A:
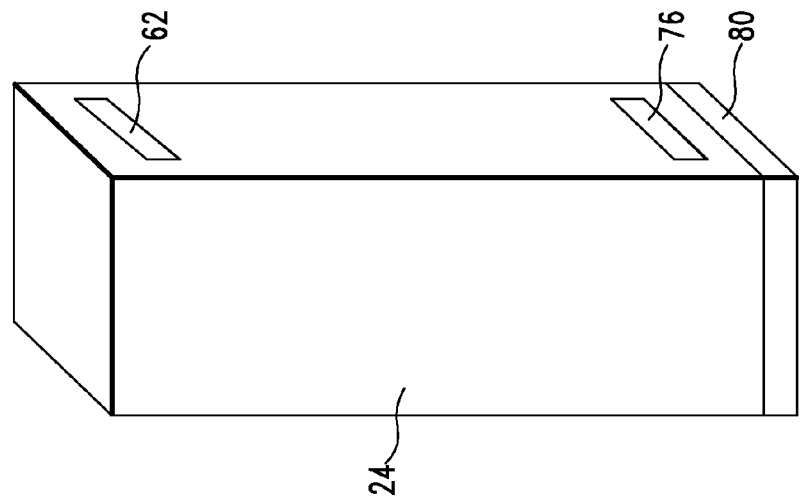
Figure 2D:
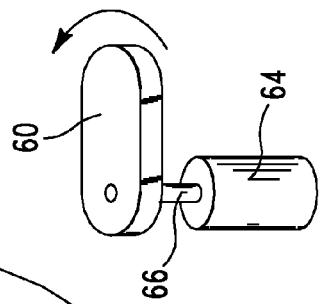
Figure 2B:
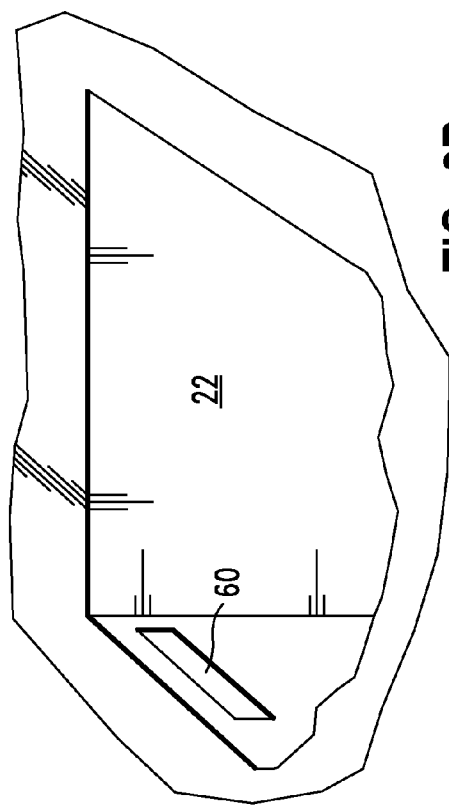
FIGS. 2b and 2c are enlarged three dimensional views of a slot of the housing of FIG. 1a showing operation of a rotating foot that locks a removable magazine into the slot.
Figure 2C:
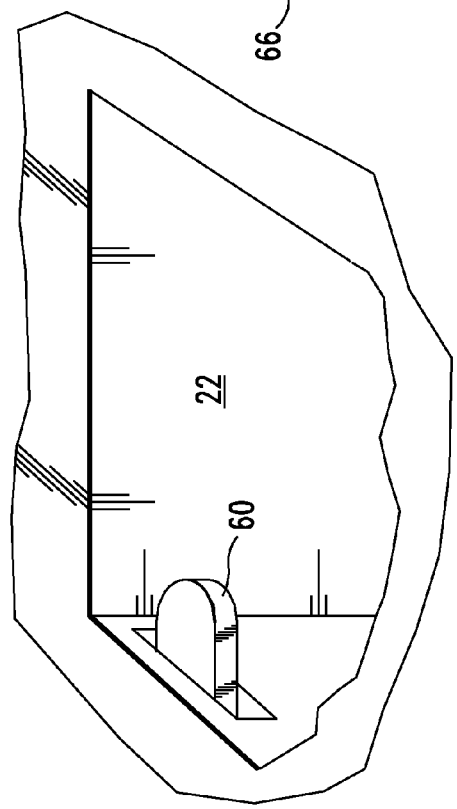
Figure 3A:
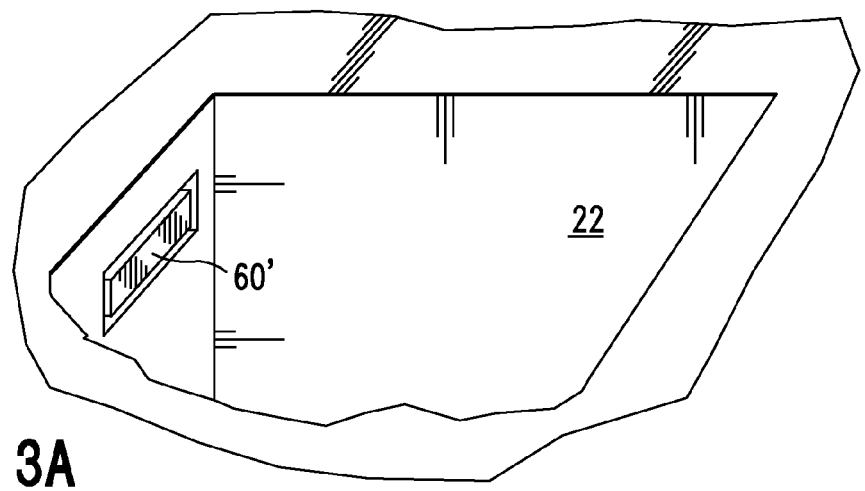
FIGS. 3a-3c are enlarged three dimensional views of a slot of the housing of FIG. 1a showing operation of another embodiment of a rotating foot that locks a removable magazine into the slot.
Figure 3B:
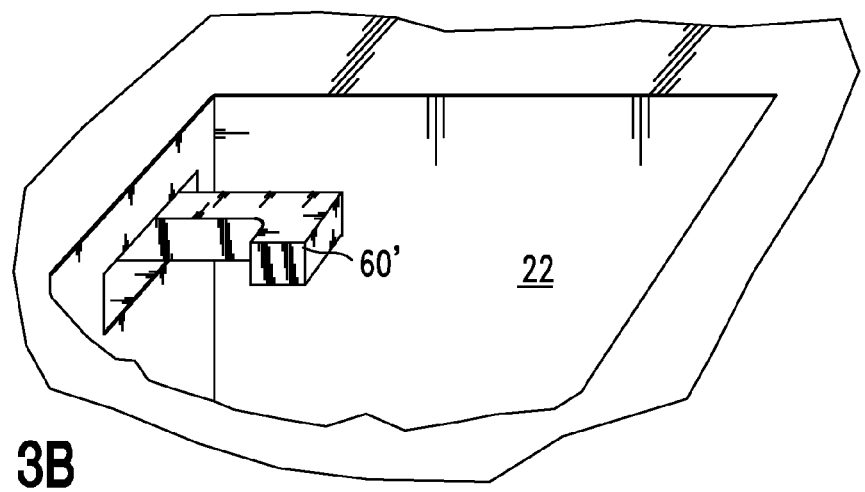
Figure 3C:
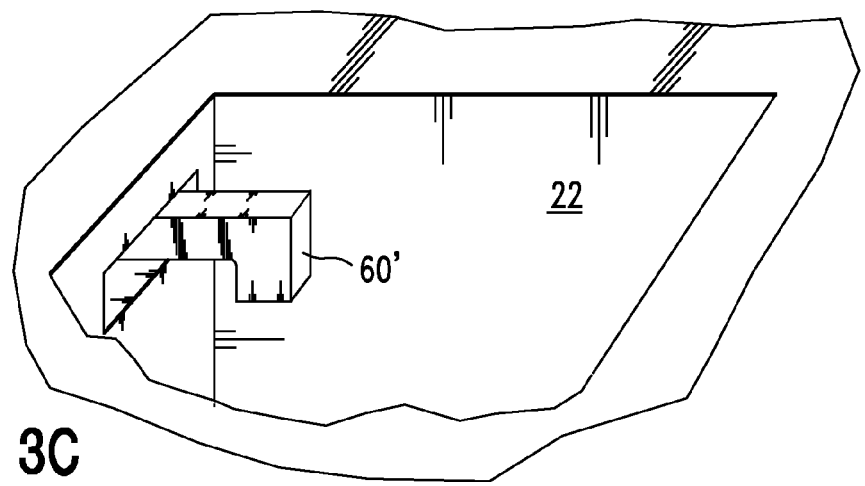

Each slot 22 for removable magazine 24 may optionally include a mechanical lock mechanism, such as rotating foot 60, that fits into opening 62 in each removable magazine 24, as shown in FIGS. 2a-2d, securely locking removable magazine 24 in place in its slot 22 in housing 20. Rotating foot 60 is controlled by motor 64 and shaft 66, as shown in FIG. 2d. An alternative way of locking removable magazine 24 in place in its slot 22 in housing 20 is shown in FIGS. 3a-3c which uses L-shaped foot 60' that rotates around an axis perpendicular to the axis of FIG. 2c.

Figure 4:
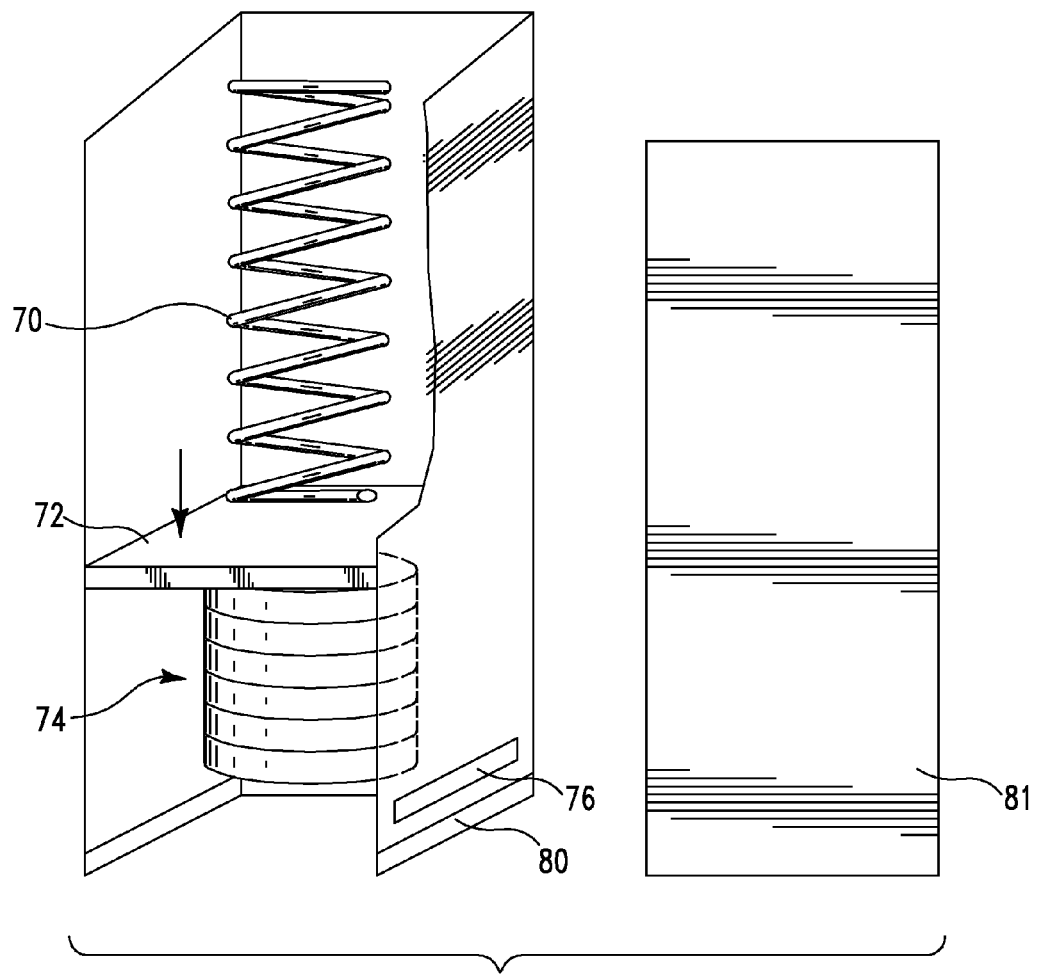

In one embodiment, removable magazine 24 includes spring 70 and pressure plate 72 that push down on pills 74, as shown in FIG. 4. Removable magazine 24 also includes sliding plate access window 76, sliding plate 78, fixed bottom plate 80 and removable back panel 81, as shown in FIGS. 4 and 5a-5f. Sliding plate 78 remains within removable magazine 24 but is operated by a pill dispensing motor through sliding plate access window 76, allowing or preventing dispensing of one or more pills.

Figure 5A:
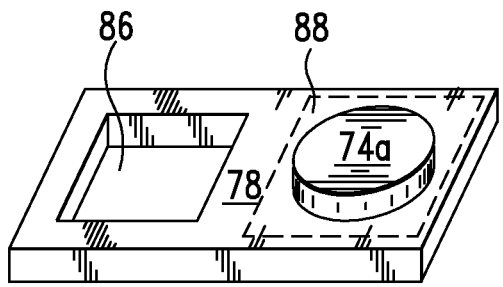
Figure 5B:
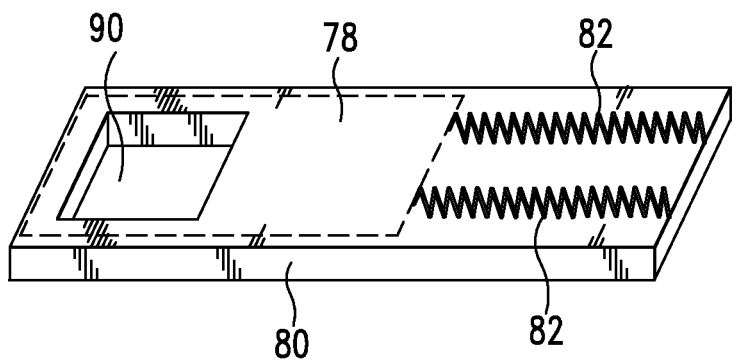
Figure 5C:
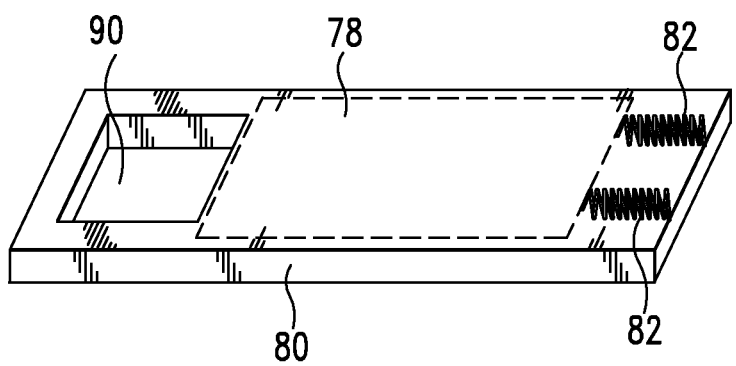
Figure 5D:
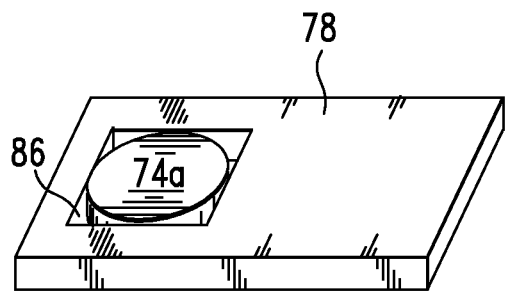
Figure 5E:
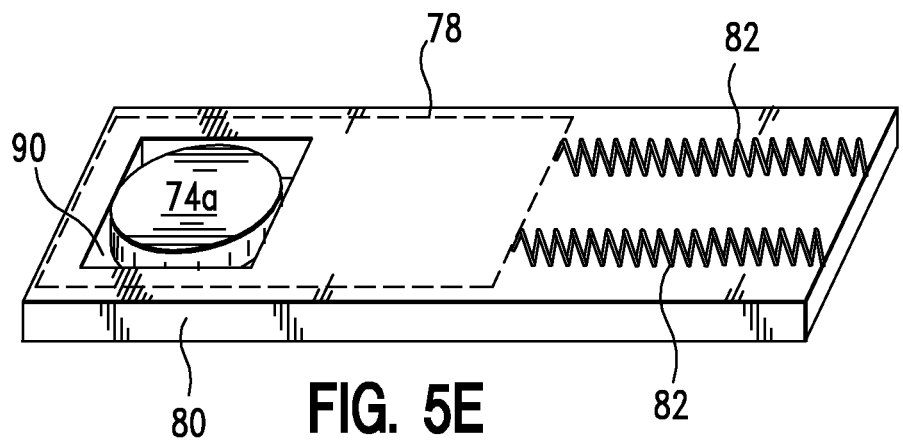
Figure 5F:
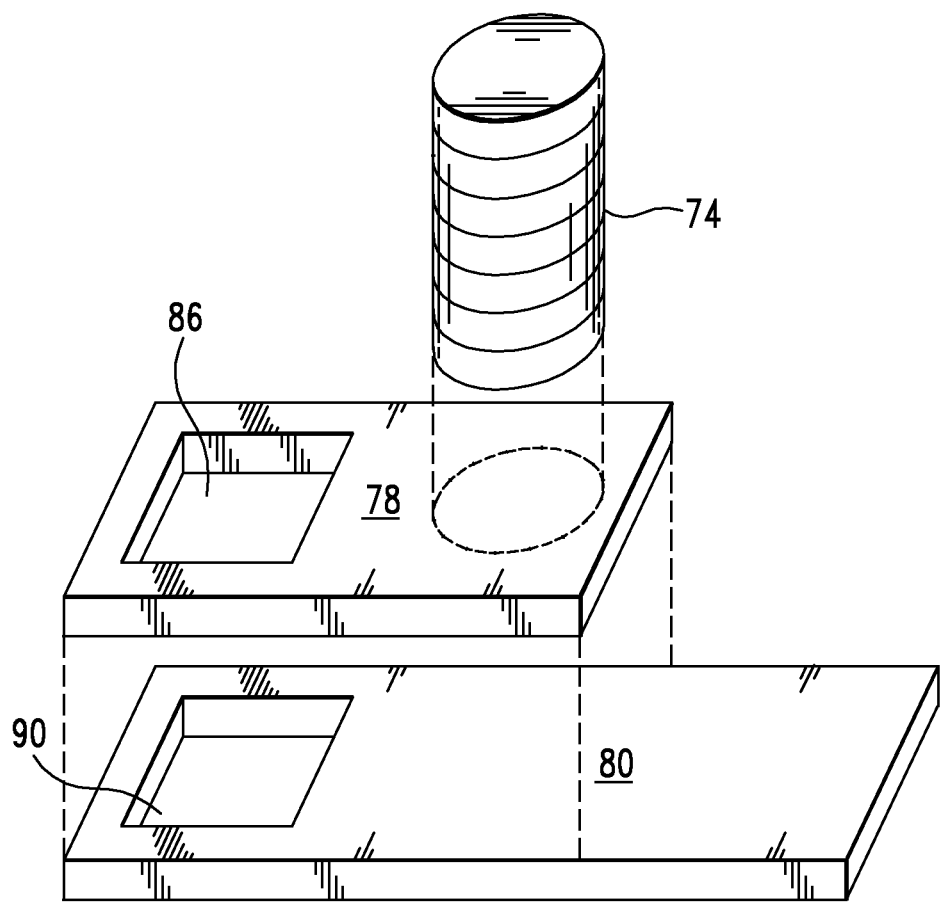

In one embodiment, sliding plate 78 of removable magazine 24 has a thickness about equal to one of pills 74a. Sliding plate 78 is positioned to the left by spring 82, as shown in FIG. 5a-5c and can be driven to the right by a motor (not shown). When sliding plate 78 is driven right by the motor and has opening 86 aligned with pill stack 74, bottom pill 74a of pill stack 74 drops into opening 86, as shown in FIG. 5d. The presence of pill 74a prevents any other pill of pill stack 74 from dropping in to opening 86. When the motor is turned off and sliding plate 78 is pushed back to the left by spring 82 only pill 74a moves to the left with opening 86, the rest of pill stack 74 remaining in place supported by planar region 88 of sliding plate 78. When opening 86 of sliding plate 78 aligns with opening 90 of fixed bottom plate 80, as shown in FIG. 5f, pill 74a then falls into opening 90 in fixed bottom plate 80, as shown in FIG. 5e, from which it is dispensed out the bottom of opening 90 by gravity and through dispensing outlet 30.

Figure 6A:
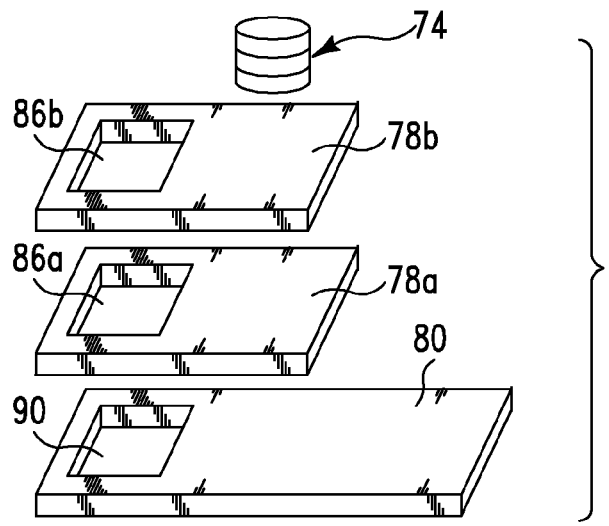
FIGS. 6a-6c are three dimensional views showing positions of two sliding plates used to dispense two pills at a time.
Figure 6B:
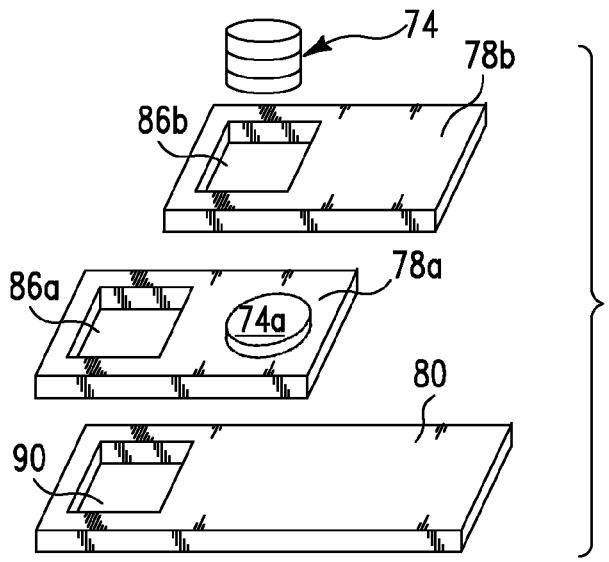
Figure 6C:
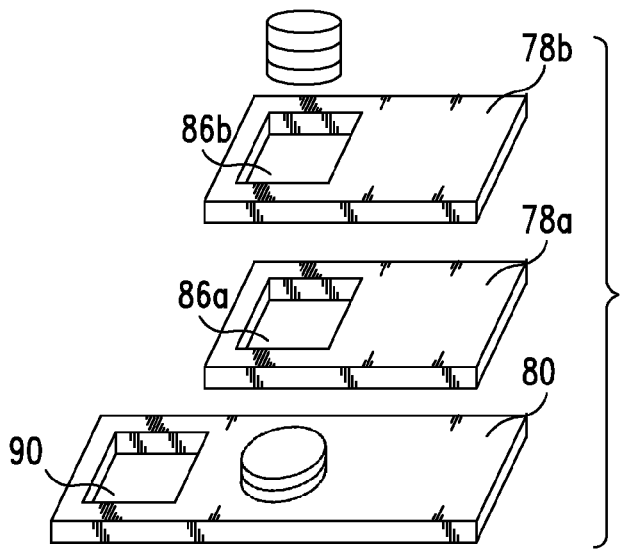

Two sliding plates could be used to allow dispensing two pills at a time, as shown in the sequence FIGS. 6a-6c. In this embodiment both sliding plates 78a, 78b move into alignment with stack of pills 74, allowing two of the stacked pills to fit into their openings, 86a, 86b. The two sliding plates then slide back into alignment with third bottom plate 80 that remains in a fixed position, allowing the two pills to fall through opening 90 in fixed bottom plate 80 for dispensing. For each additional pill desired for dispensing another sliding plate can be included. Alternatively, two stacks of pills can be mounted over each plate and each plate can have two openings to accept a pill from each stack. In another alternative, sliding plate 78 can slide back and forth multiple times.

Figure 7:
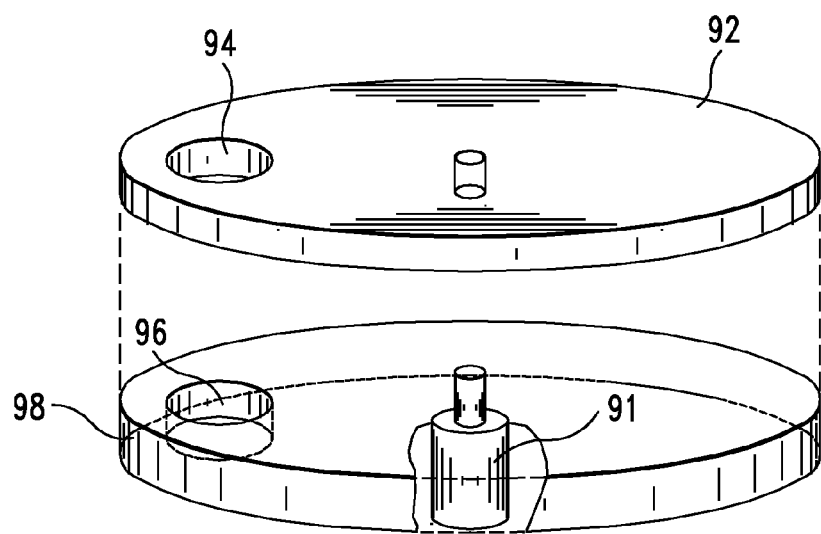
FIG. 7 is a three dimensional view of another embodiment in which a rotating plate is used to dispense a pill.

In another embodiment, motor 91 operates a rotating plate 92 that has opening 94 for a pill, but no springs, as shown in FIG. 7. Opening 94 in rotating plate 92 receives a pill when aligned with stack of pills 74 and dispenses the pill when opening 94 in rotating plate 92 is aligned with opening 96 in fixed bottom plate 98 below. Multiple openings can be provided in plate 92 to dispense multiple pills. Alternatively, rotating plate 92 can rotate multiple times to dispense multiple pills.

Figure 8:
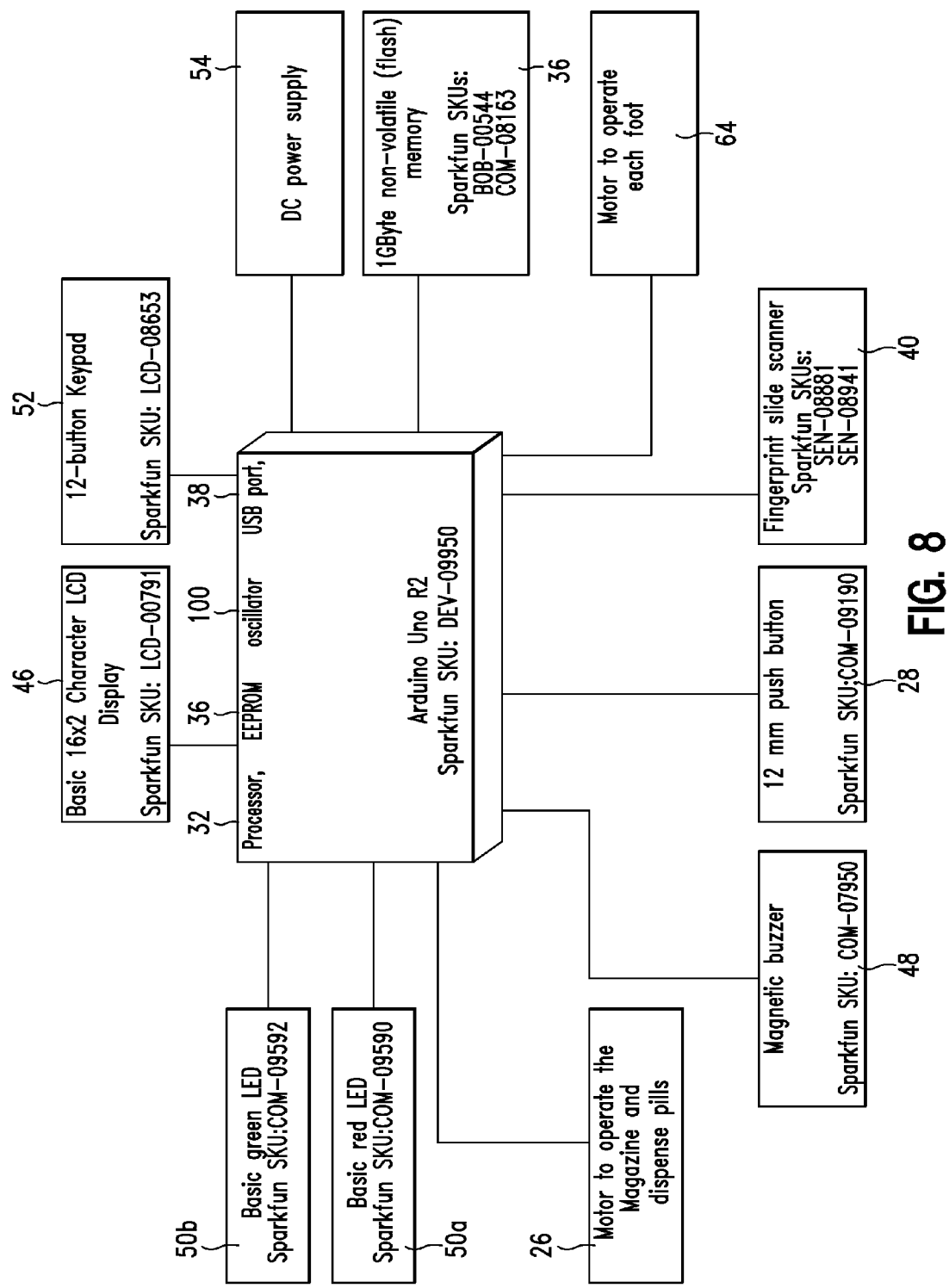
FIG. 8 is a block diagram of one embodiment of the electronic circuit of FIG. 1a, including a central processing unit that includes non-volatile memory, an oscillator, and a USB port as well as connections to the central processing unit for the dispense motor that operates the removable magazine lock, the push button, the fingerprint slide scanner, the LCD screen, the buzzer, the LEDs, the keypad, and the power supply.

One embodiment of electronic circuit 32 is shown in the block diagram of FIG. 8. Central processing unit 34 includes non-volatile memory 36, oscillator 100, and USB port 38. Connections to central processing unit 34 are provided for dispense motor 26 to operate the removable magazine lock, push button 28, fingerprint slide scanner 40, LCD screen 46, buzzer 48, LEDs 50a, 50b, keypad 42, and power supply 54.

A strong case fabricated of polycarbonate, carbon fiber, aluminum, or another material may be used to prevent tampering. Wire mesh incorporated in the casing may be used to prevent unauthorized communication through the housing. Sensors such as accelerometers, temperature sensors, moisture sensors, and Global Positioning System (GPS), may be included to detect tampering and may be connected to central processing unit 34. Other sensors for detecting holes or other physical compromise of the wire mesh in the case also may be included, or to otherwise detect tampering, such as those described in U.S. Pat. No. 4,593,384 and in "Thinking inside the box: system-level failures of tamper proofing," by Saar Drimer, Steven J. Murdoch, and Ross Anderson, University of Cambridge Computer Laboratory Technical Report UCAM-CL-TR-711, ISSN 1476-2986, February 2008 and in "Physical security devices for computer subsystems: a survey of attacks and defences", by Steve H. Weingart, *Cryptographic Hardware and Embedded Systems Workshop*, volume 1965 of LNCS, pages 302-317, London, UK, August 2000, Springer-Verlag. In one embodiment electronic circuit 32 or magazine 24 also includes a memory for logging information about such detected tampering. Magazine 24 or housing 20 may also include a communications device connected to communicate information about the tampering. Communications devices, such as USB, Firewire, Wi-Fi, Blue tooth, GSM, 3G/4G, wireless USB, and mobile ad-hoc networks can be used. A GPS device can be included in magazine 24 or housing 20 for theft tracking Magazine 24 or housing 20 may include a local alerting device connected to alert in response to the tampering, such as a buzzer alarm, a projector or a local display.

Figure 10:
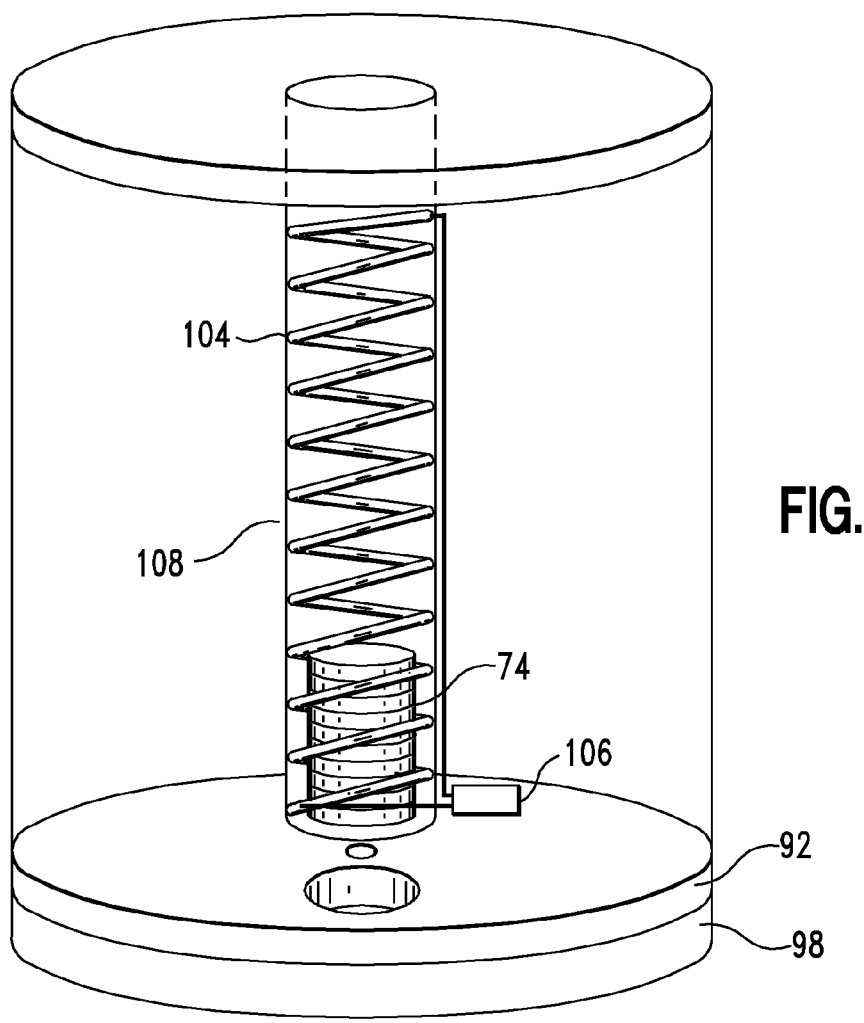
FIG. 10 is a three dimensional view of a removable magazine with another embodiment of a pill destroying device that includes a metal coil that provides sufficient heat when current from a battery flows to denature pills held in place in its pill sleeve.
Figure 9A:
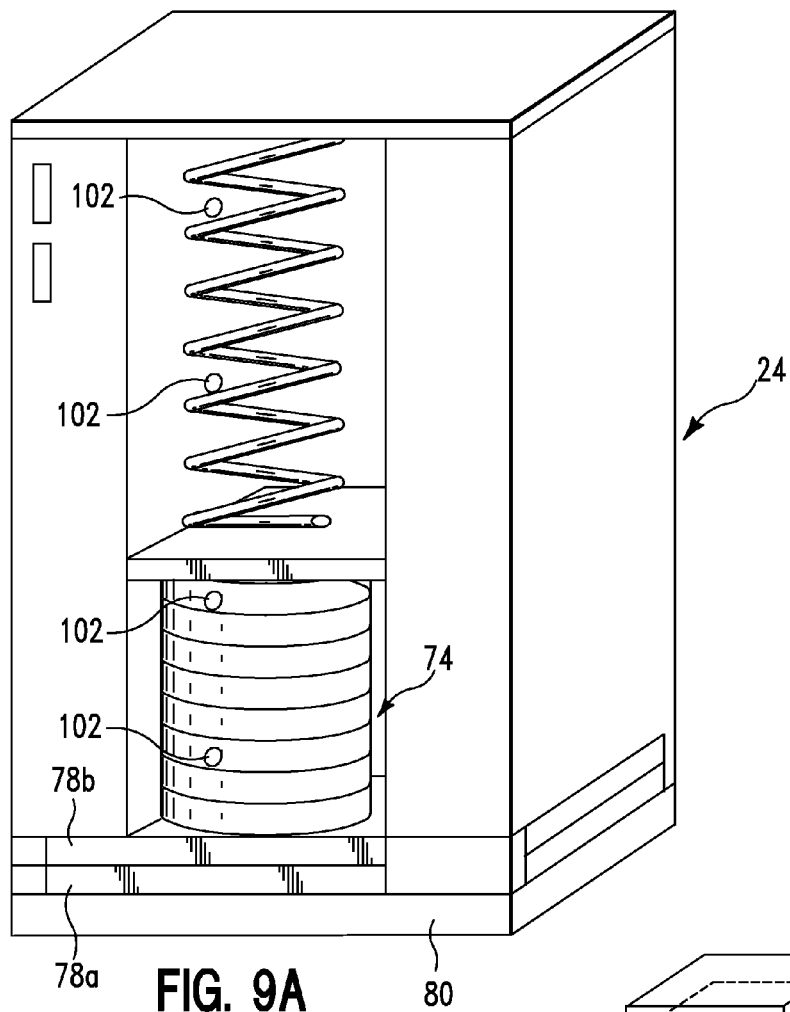
FIGS. 9a-9b are three dimensional views of a removable magazine for use with the housing of FIG. 1a that includes a pill destroying device connected to destroy the pills in response to detected tampering.
Figure 9B:
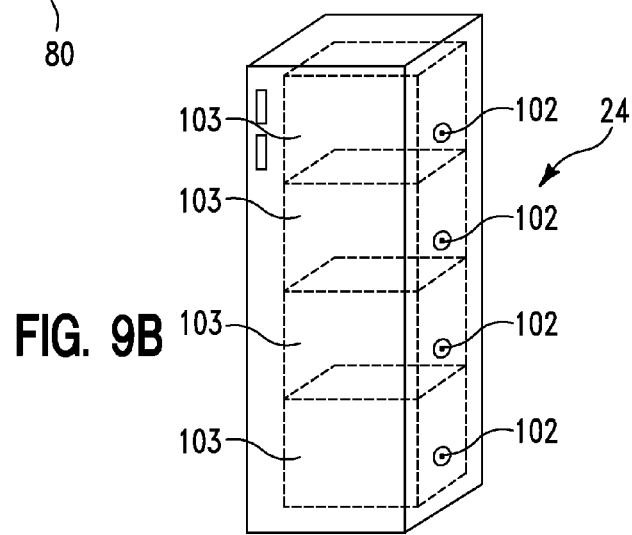

Magazine 24 or housing 20 can include a pill destroying device connected to destroy the pills in response to detected tampering. In one embodiment, the pill destroying device includes pressurized liquid denaturant from reservoirs 103 with nozzles 102 positioned to spray the liquid over pills in the magazine, as shown in FIGS. 9a-9b. Denaturants can be used to inactivate the medication, render the medication unfit for consumption, or increase the difficulty of extracting the active compounds from the pills. Liquid denaturants include, but are not limited to hydrogen peroxide, sulfuric acid, and hydrochloric acid. The selection of the most appropriate denaturant will depend on the chemical makeup of the pills and the design of the magazine and device housing. In another embodiment, the pill destroying device includes metal coil 104 that provides sufficient heat when current from battery 106 flows to denature pills 74 held in place in pill sleeve 108, as shown in FIG. 10. Each of these pill destroying techniques can be provided alone. Some can be used in combination with others.

Figure 11A:
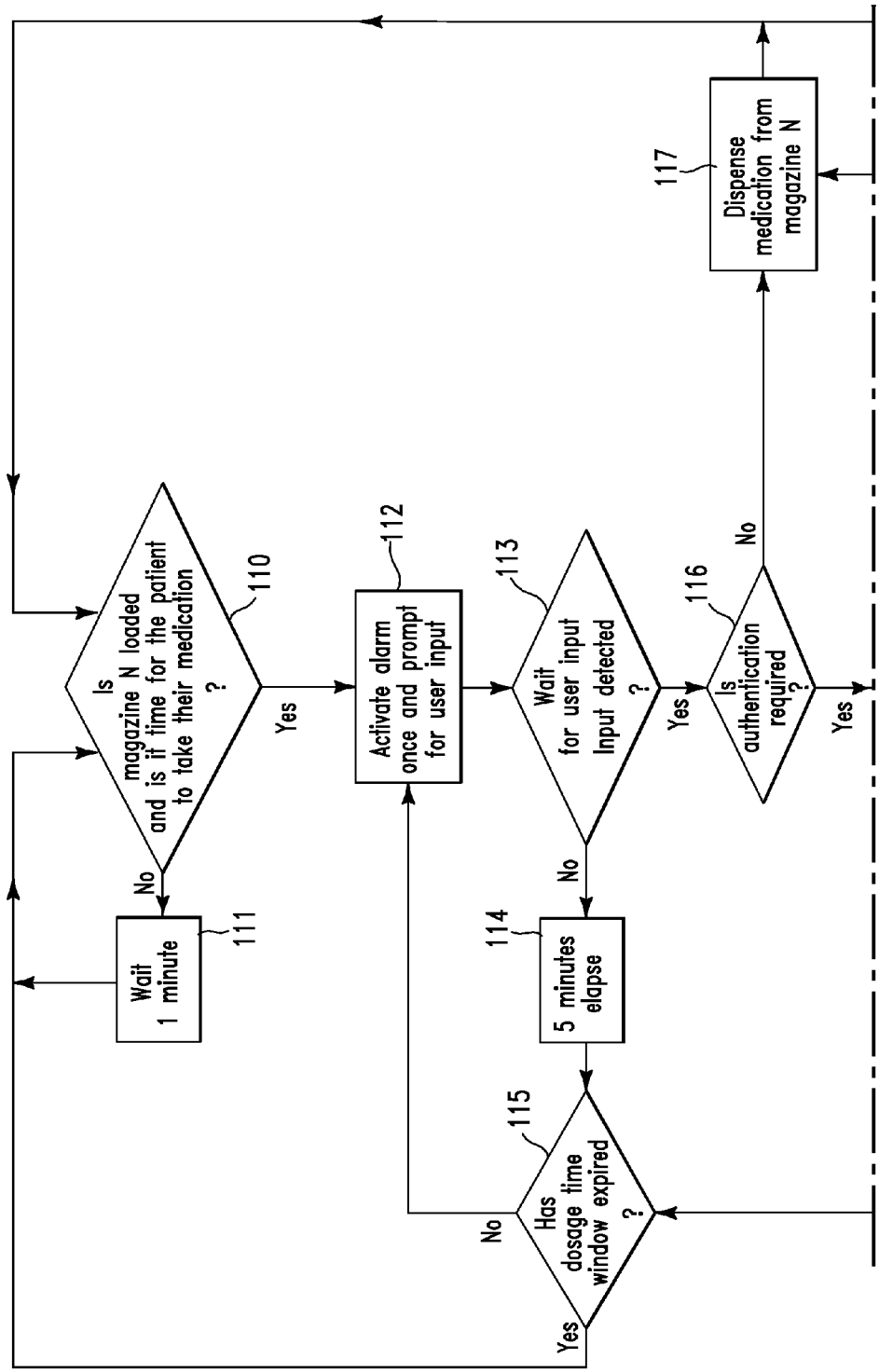

In one embodiment, operation of the device follows a process along the lines of the program shown in the flow chart of FIG. 11 for each removable magazine 24 that may be inserted into housing 20. Central processing unit 34 determines whether or not magazine 24n is loaded into housing 30 by evaluating the state of button 84, as shown in box 110. If so, CPU 34 determines whether it is time for the patient to take his or her medication from that magazine 24n, as also shown in box 110. If not, CPU 34 waits a pre-programmed time, such as 1 minute, as shown in box 111. After that pre-programmed time, CPU 34 asks the same questions again. If magazine 24n is loaded and it is time for the patient to take a pill from that magazine 24n, CPU 34 activates an alarm to prompt the user for user input, as shown in box 112.

CPU 34 then waits for user input, as shown in box 113. CPU 34 waits another pre-programmed time, such as 5 minutes, as shown in box 114, and determines whether the dosage time window has been exceeded, as shown in box 115. The dosage time window is the time after which the dosage should be skipped. If the dosage time window has been exceeded and the user has not responded, then CPU 34 does not prompt the user anymore and begins again to determine whether the next time for taking a dose has arrived. If the dosage time window has not been exceeded and the user has not responded, then CPU 34 activates the alarm again and prompts the user again, and waits for user input again, as shown in boxes 112 and 113.

If user input is detected, such as by the user pressing button 28, CPU 34 determines whether authentication is required, as shown in box 116. If no authentication is required, then the medication is dispensed from removable magazine 24n, as shown in box 117. CPU 34 then begins again to determine whether the next time for taking a dose has arrived, as shown in box 110.

If authentication is required, then CPU 34 determines whether a user authentication input corresponds to the correct patient, as shown in box 118. If the correct user authentication is detected, then the medication is dispensed from removable magazine 24n, as shown in box 117. CPU 34 then begins again to determine whether the next time for taking a dose has arrived, as shown in box 110.

If the correct user authentication is not detected, CPU 34 determines whether a user has tried and failed to authenticate a specified number of times, such as 3 times, as shown in box 119. If CPU 34 determines that the user has tried and failed to authenticate the specified number of times, CPU 34 sends a message to display 46 indicating failed authentication, as shown in box 120. In this case CPU 34 waits a pre-specified time, such as two minutes, as shown in box 121, and then CPU 34 checks whether the dosage time window has expired as shown in box 115. If CPU 34 determines that the user has not used up all the specified number of tries, CPU 34 checks whether the dosage time window has expired as shown in box 122. If not, CPU 34 prompts the user to re-enter authentication credentials and CPU 34 again determines whether the user has tried and failed to authenticate the specified number of times. In any case in which the dosage time window has expired CPU 34 then begins again to determine whether the next time for taking a dose has arrived, as shown in box 110.

Figure 12A:
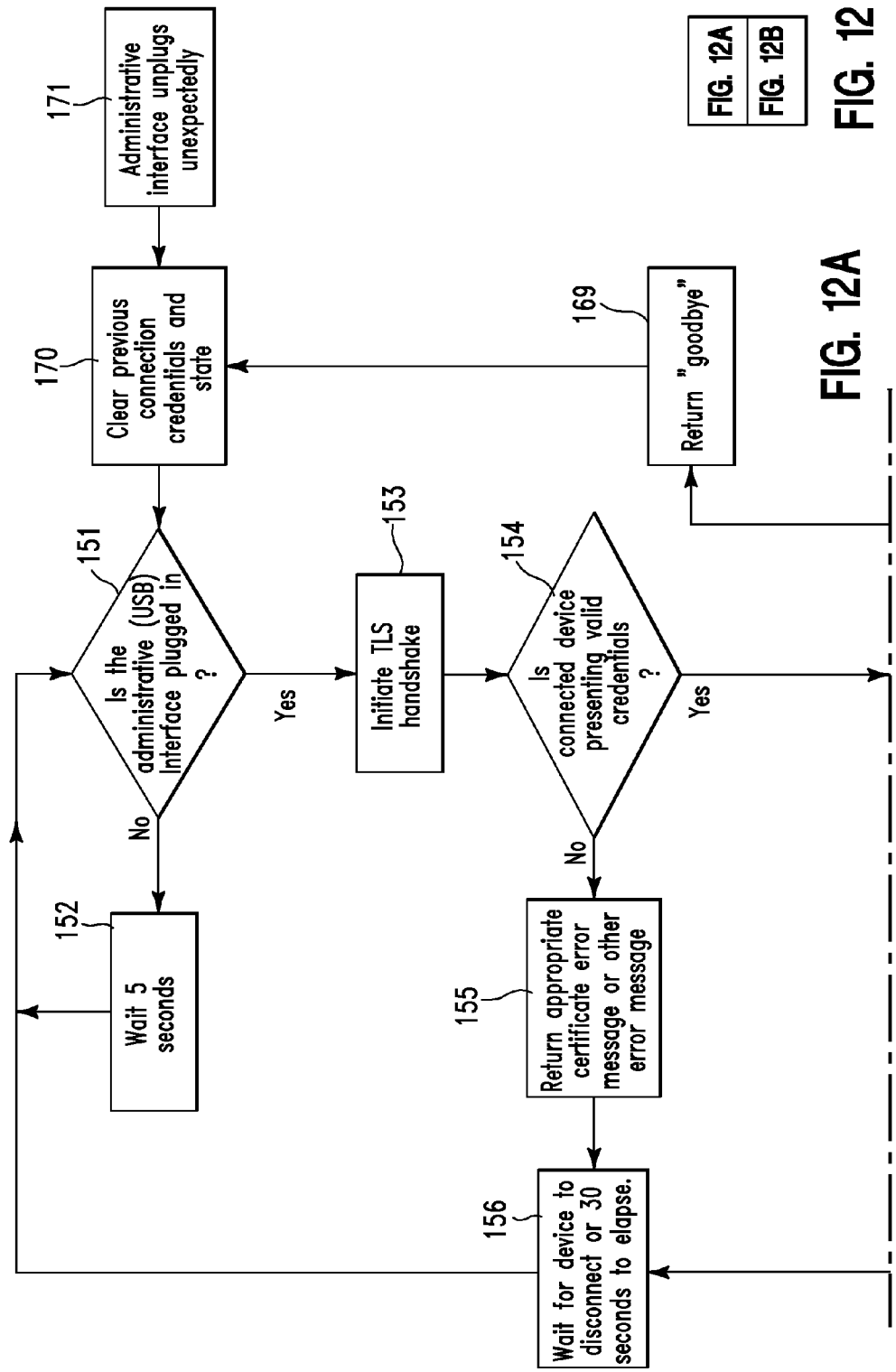
FIGS. 12a-12b, is a flow chart showing a program for limited to authorized personnel the ability to remove a removable magazine from the housing and to insert a removable magazine into the housing.
Figure 12B:
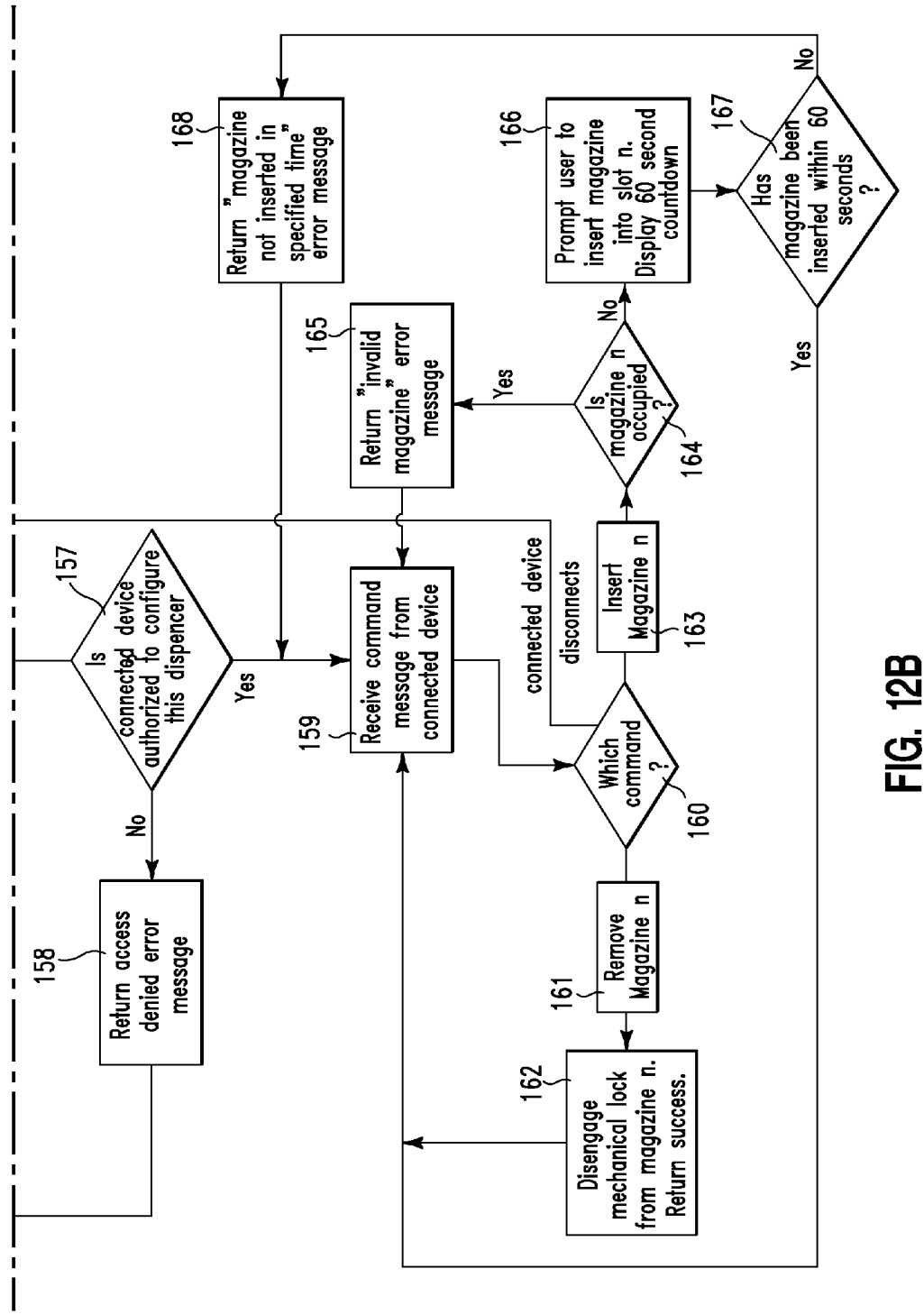

Removal of removable magazine 24 from housing 20 and insertion of removable magazine 24 into housing 20 may be limited to authorized personnel, such as a pharmacist, who has the proper software and credentials, as shown in the flow chart in FIG. 12.

CPU 34 determines whether or not an administrative device, such as a notebook computer, desktop computer, tablet computer, server, mainframe, smartphone, or other electronic or digital device is plugged into the micro-USB interface or otherwise is in communication with CPU 34, as shown in box 151. If no such device is connected, CPU 34 waits for a pre-specified time, such as five seconds, as shown in box 152 then again determines whether or not an administrative device is in communication, as shown in box 151. If an administrative device is in communication, CPU 34 initiates a secure network authentication/encryption protocol, such as Transport Layer Security (TLS) or Secure Sockets Layer (SSL) with the administrative device, as shown in box 153. The results of the secure network authentication/encryption protocol are evaluated to determine whether the administrative device presented valid credentials, as shown in box 154.

If the administrative device did not present valid credentials or if some other error prevents correct negotiation, CPU 34 provides a certificate error message or another error message to the administrative device and the error message may also be displayed on LCD screen 46, as shown in box 155. CPU 34 waits for the administrative device to disconnect or waits a pre-specified time, such as thirty seconds, as shown in box 156, and when one of these is satisfied, then again determines whether or not an administrative device is in communication, as shown in box 151.

If the administrative device did present valid credentials, CPU 34 then determines whether the authenticated administrative device is authorized to configure this pill dispenser, as shown in box 157.

If the authenticated administrative device is not authorized to configure this pill dispenser, CPU 34 returns an "access denied" or similar error message, or turns on the red LED light, as shown in box 158. CPU 34 then waits for the administrative device to disconnect or waits a pre-specified time, such as thirty seconds, as shown in box 156, and when one of these is satisfied, then again determines whether or not an administrative device is in communication, as shown in box 151.

If the authenticated administrative device is authorized to configure this pill dispenser, CPU 34 waits for the connected authenticated administrative device to send a command. Once it receives a command, as shown in box 159, CPU 34 decodes the command, as shown in box 160 and handles it appropriately. For example, if the connected authenticated administrative device requests to "Remove Magazine 24n", as shown in box 161, CPU 34 sends a command to operate the motor controlling mechanical lock 60 so as to disengage mechanical lock 60 from magazine 24n and returns "success," or "magazine unlocked" or a similar message indicating success to the LCD screen or turns on the green LED light, as shown in box 162. CPU 34 then waits for the connected authenticated administrative device to send another command.

If the connected authenticated administrative device requests to "Insert Magazine 24n", as shown in box 163, CPU 34 detects that magazine 24n is currently inserted when the inserted magazine depresses button 84. If slot n for magazine 24n is currently occupied, as shown in box 164, CPU 34 returns an "invalid magazine" or similar appropriate error message, as shown in box 165, to await another command. If CPU 34 determines that magazine slot n is not occupied, CPU 34 prompts the user to insert a magazine into slot 24n and displays a pre-determined timed countdown, such as a 60 second countdown on LCD screen 46, as shown in box 166. CPU 34 then detects whether or not magazine 24n is currently inserted and was inserted within the time limit by evaluating the state of button 84, as shown in box 167. If no magazine has been inserted, CPU 34 displays an error message, such as "magazine not inserted in specified time," as shown in box 168. Regardless of whether the magazine has been inserted successfully or not, CPU 34 awaits receipt of a new command, as shown in box 159.

If the connected authenticated administrative device requests to "disconnect" displays "goodbye" on LCD screen 46 as shown in box 169. CPU 34 then clears and re-initializes all connection-related credentials, as shown in box 170, and again determines whether or not an administrative device is in communication, as shown in box 151. If at any point in this process, the connected authenticated administrative device unexpectedly unplugs, as shown in box 171, CPU 34 then clears and re-initializes all connection-related credentials, as shown in box 170, and again determines whether or not an administrative device is in communication, as shown in box 151.

While several embodiments, together with modifications thereof, have been described in detail herein and illustrated in the accompanying drawings, it will be evident that various further modifications are possible without departing from the scope of the invention as defined in the appended claims. Nothing in the above specification is intended to limit the invention more narrowly than the appended claims. The examples given are intended only to be illustrative rather than exclusive.

What is claimed is:

1. A dispensing device for dispensing pills, comprising a housing and a removable magazine, wherein said housing is configured for holding said removable magazine, wherein said removable magazine is configured for holding the pills in a column arrangement, and wherein said housing includes:
    a dispensing unit configured to operate on at least one pill in said column arrangement in said removable magazine to dispense said at least one pill, wherein, as dispensed, said at least one pill is unpackaged, wherein said dispensing unit includes a moveable plate having a thickness about equal to thickness of said pill, wherein said plate includes an opening into which said one pill may enter, wherein presence of said one pill in said opening blocks another pill from entering into said opening wherein said opening extends entirely through said moveable plate; and
    an electronic circuit that provides a signal to activate the dispensing unit to dispense said at least one pill at each of a plurality of pre-specified dosing times.

2. A dispensing device as recited in claim 1, wherein said removable magazine includes a device configured to remove exclusively one pill from the column of pills at a time.

3. A dispensing device as recited in claim 1, wherein said removable magazine is configured for holding the pills in a column arrangement of otherwise loose pills.

4. A dispensing device as recited in claim 1, further comprising a plurality of said removable magazines, wherein said housing is configured for holding said plurality of said removable magazines.

5. A dispensing device as recited in claim 4, wherein each removable magazine of said plurality of removable magazines is configured to hold a different kind of pill.

6. A dispensing device as recited in claim 4, wherein each of said removable magazines is configured to hold a sufficient number of pills of a single type to provide a specified dose at each of said plurality of dosing times.

7. A dispensing device as recited in claim 1, wherein said column is vertical when said removable magazine is in said housing.

8. A dispensing device as recited in claim 7, wherein said removable magazine includes a device configured to remove exclusively one pill from the column of pills at a time.

9. A dispensing device for dispensing doses of pills at a plurality of pre-specified dosing times, comprising a housing and a removable magazine, wherein said housing is configured for holding said removable magazine, wherein said removable magazine is configured for holding the pills in a column arrangement, and wherein said housing includes:
   a dispensing unit connected to receive a signal to activate said dispensing unit at the plurality of dosing times, wherein said dispensing unit is configured to operate on at least one pill in said column arrangement in said in said removable magazine to dispense said at least one pill when activated by said signal, wherein when dispensed, said at least one pill is unpackaged; and
   a tamper recognizing device and a pill destroying device, wherein said tamper recognizing device is configured to recognize the occurrence of tampering and wherein said pill destroying device is connected to destroy the pills in response to tampering.

10. A dispensing device as recited in claim 9, wherein said housing further comprises at least one from the group consisting of a memory for logging said tampering, a communications device connected to communicate information about said tampering, and a local alerting device connected to alert in response to said tampering.

11. A dispensing device as recited in claim 9, further comprising an authentication device connected for receiving identifying data from the current user, comparing said current user identifying data with previously stored identifying data, and authorizing said dispensing said dose to the current user if said current user identifying data sufficiently matches said previously stored identifying data.

12. A dispensing device as recited in claim 9, wherein said column is vertical when said removable magazine is in said housing.

13. A dispensing device as recited in claim 9, wherein said removable magazine is configured for holding the pills in a column arrangement of otherwise loose pills.

14. A dispensing device as recited in claim 9, wherein said device includes a moveable plate having a thickness about equal to thickness of said pill, wherein said plate includes an opening into which said one pill may enter, wherein presence of said one pill in said opening blocks another pill from entering into said opening wherein said opening extends entirely through said moveable plate.

15. A dispensing device as recited in claim 14, wherein said removable magazine includes a device configured to remove exclusively one pill from the column of pills at a time.

* * * * *